(12) United States Patent
Zhu (10) Patent No.: US 12,428,468 B2
(45) Date of Patent: Sep. 30, 2025

(54) HUMAN COLLAGEN 17-TYPE POLYPEPTIDE, PRODUCTION METHOD THEREFOR AND USE THEREOF

(71) Applicant: SHANXI JINBO BIO-PHARMACEUTICAL CO., LTD., Shanxi (CN)

(72) Inventor: Yun Zhu, Beijing (CN)

(73) Assignee: SHANXI JINBO BIO-PHARMACEUTICAL CO., LTD., Taiyuan (CN)

( * ) Notice: Subject to any disclaimer, the term of this patent is extended or adjusted under 35 U.S.C. 154(b) by 0 days.

(21) Appl. No.: 18/612,612

(22) Filed: Mar. 21, 2024

(65) Prior Publication Data
US 2024/0309067 A1   Sep. 19, 2024

Related U.S. Application Data

(63) Continuation of application No. 17/761,992, filed as application No. PCT/CN2020/123600 on Oct. 26, 2020, now Pat. No. 12,043,657.

(30) Foreign Application Priority Data

Oct. 31, 2019   (CN) .......................... 201911051106.3

(51) Int. Cl.
| | | |
|---|---|---|
| C07K 14/78 | (2006.01) | |
| A61K 8/65 | (2006.01) | |
| A61Q 19/00 | (2006.01) | |
| A61K 38/00 | (2006.01) | |

(52) U.S. Cl.
CPC .............. C07K 14/78 (2013.01); A61K 8/65 (2013.01); A61Q 19/00 (2013.01); *A61K 38/00* (2013.01)

(58) Field of Classification Search
CPC .................. C07K 14/78; A61K 8/65
See application file for complete search history.

(56) References Cited

U.S. PATENT DOCUMENTS

| | | | | |
|---|---|---|---|---|
| 2002/0081659 A1* | 6/2002 | Rosen | ............... | C07K 14/4702 |
| | | | | 435/7.1 |
| 2007/0083334 A1* | 4/2007 | Mintz | ................... | G16B 40/00 |
| | | | | 702/19 |
| 2013/0237486 A1 | 9/2013 | Bella | | |

FOREIGN PATENT DOCUMENTS

| | | |
|---|---|---|
| CN | 110845603 A | 2/2020 |
| WO | 2012063088 A2 | 5/2012 |
| WO | 2019057704 A1 | 3/2019 |

OTHER PUBLICATIONS

Li, Kehua et al., "Genomic organization of collagenous domains and chromosomal assignment of human 180-kDa bullous pemphigoid antigen-2 a novel collagen of stratified squamous epithelium", The Journal of Biological Chemistry, vol. 266, No. 35, pp. 24064-24069 (Dec. 15, 1991).

Yao, Juming et al., "Design, Expression and Characterization of Collagen-Like Proteins Based on the Cell Adhesive and Crosslinking Sequences Derived from Native Collagens", The Japanese Biochemical Society, vol. 136, No. 5, pp. 643-649 (2004).

Areida, Sayed K. et al., "Properties of the Collagen Type XVII Ectodomain", The Journal of Biological Chemistry, vol. 276, No. 12, pp. 1594-1601 (2001).

\* cited by examiner

*Primary Examiner* — Amber D Steele
(74) *Attorney, Agent, or Firm* — Lando & Anastasi, LLP (57) ABSTRACT

Provided is a polypeptide, a production method therefor and a use thereof. The polypeptide includes 63 to 1496 continuous amino acid residues of SEQ ID NO: 9, and includes a sequence represented by $(A)_m$ or is composed of the sequence represented by $(A)_m$, wherein each A is an amino acid sequence selected from any one of those represented by SEQ ID NO: 1, SEQ ID NO: 2 and SEQ ID NO: 3, or a modified amino acid sequence or a sequence variant thereof; m is an integer between 1 and 10; and each A is the same or different and two adjacent As are directly connected by peptide bonds or connected by at least one amino acid residue, wherein the polypeptide has a cell adhesion activity, and a method of producing said polypeptide and use of said polypeptide.

20 Claims, 2 Drawing Sheets

Specification includes a Sequence Listing.

SEQUENCE LISTING

```
Sequence total quantity: 9
SEQ ID NO: 1            moltype = AA  length = 69
FEATURE                 Location/Qualifiers
REGION                  1..69
                        note = C17A
```

```
source                   1..69
                         mol_type = protein
                         organism = synthetic construct
SEQUENCE: 1
GSPGPKGDMG SPGPKGDRGF PGTPGIPGPL GHPGPQGPKG QKGSVGDPGM EGPMGQRGRE   60
GPMGPRGEA                                                           69

SEQ ID NO: 2             moltype = AA   length = 63
FEATURE                  Location/Qualifiers
REGION                   1..63
                         note = C17B
source                   1..63
                         mol_type = protein
                         organism = synthetic construct
SEQUENCE: 2
GLQGLRGEVG LPGVKGDKGP MGPPGPKGDQ GEKGPRGLTG EPGMRGLPGA VGEPGAKGAM   60
GPA                                                                 63

SEQ ID NO: 3             moltype = AA   length = 119
FEATURE                  Location/Qualifiers
REGION                   1..119
                         note = C17C1
source                   1..119
                         mol_type = protein
                         organism = synthetic construct
SEQUENCE: 3
GADFAGDLDY NELAVRVSES MQRQGLLQGM AYTVQGPPGQ PGPQGPPGIS KVFSAYSNVT   60
ADLMDFFQTY GAIQGPPGQK GEMGTPGPKG DRGPAGPPGH PGPPGPRGHK GEKGDKGDQ   119

SEQ ID NO: 4             moltype = AA   length = 207
FEATURE                  Location/Qualifiers
REGION                   1..207
                         note = C17A3
source                   1..207
                         mol_type = protein
                         organism = synthetic construct
SEQUENCE: 4
GSPGPKGDMG SPGPKGDRGF PGTPGIPGPL GHPGPQGPKG QKGSVGDPGM EGPMGQRGRE   60
GPMGPRGEAG SPGPKGDMGS PGPKGDRGFP GTPGIPGPLG HPGPQGPKGQ KGSVGDPGME  120
GPMGQRGREG PMGPRGEAGS PGPKGDMGSP GPKGDRGFPG TPGIPGPLGH PGPQGPKGQK  180
GSVGDPGMEG PMGQRGREGP MGPRGEA                                     207

SEQ ID NO: 5             moltype = DNA   length = 621
FEATURE                  Location/Qualifiers
misc_feature             1..621
                         note = C17A3-DNA
source                   1..621
                         mol_type = other DNA
                         organism = synthetic construct
SEQUENCE: 5
ggtagcccag gtccaaaagg tgatatggga agcccaggtc cgaaaggtga tcgtggtttt   60
ccgggtacac caggtattcc gggtccactg ggtcatccag gtccgcaagg tccgaaaggc  120
cagaaaggta gcgtgggtga tccgggtatg gaagggccta ggggcagcg tgggcgtgaa  180
gggccgatgg gtccgcgtgg tgaagcaggt agcccgggc ctaaagggga tatgggagt   240
ccgggtccga aagggatcg tggatttccg ggtacgccgg gtatcccggg tccgctgggt  300
catccgggtc cgcaagggcc taaaggtcag aaaggtagtg tgggtgatcc tggtatggaa  360
ggtccgatgg gtcagcgtgg tcgtgagggt ccgatgggac cgcgtggtga ggctggtagc  420
cctggtccga aggagatat gggtagcccg gtccgaaag tgaccgtgg ttttcctggt   480
acaccgggta ttcagggcc tctgggtcat cctggtcctc agggtccgaa aggtcagaaa  540
gggagtgtgg gagatccggg tatggagggt ccgatgggc agcgcggtcg tgaaggtccg  600
atgggcccgc gtggtgaagc c                                           621

SEQ ID NO: 6             moltype = AA   length = 189
FEATURE                  Location/Qualifiers
REGION                   1..189
                         note = C17B3
source                   1..189
                         mol_type = protein
                         organism = synthetic construct
SEQUENCE: 6
GLQGLRGEVG LPGVKGDKGP MGPPGPKGDQ GEKGPRGLTG EPGMRGLPGA VGEPGAKGAM   60
GPAGLQGLRG EVGLPGVKGD KGPMGPPGPK GDQGEKGPRG LTGEPGMRGL PGAVGEPGAK  120
GAMGPAGLQG LRGEVGLPGV KGDKGPMGPP GPKGDQGEKG PRGLTGEPGM RGLPGAVGEP  180
GAKGAMGPA                                                         189

SEQ ID NO: 7             moltype = DNA   length = 567
FEATURE                  Location/Qualifiers
misc_feature             1..567
                         note = C17B3-DNA
```

```
source                  1..567
                        mol_type = other DNA
                        organism = synthetic construct
SEQUENCE: 7
ggtctgcagg gtctgcgtgg tgaagtagga ctgccgggtg tgaaaggaga taaaggacca    60
atgggtccac caggaccaaa aggagatcaa ggagaaaaag gaccacgtgg tctgacaggt   120
gaaccgggta tgcgtgggct gccgggagca gttggagaac cgggagcaaa aggagcaatg   180
ggtccagcag gactgcaggg tctgcgcggt gaagtggcac tgcctggtgt taaaggggat   240
aaagggccga tgggtccgcc gggtccgaaa ggagatcagg gagaaaaagg gccgcgtggt   300
ctgaccggtg aacgggaat gcgtggtctg ccgggggctg tgggtgagcc aggtgcaaaa   360
ggtgcaatgg gtcctgcagg tctgcaagga ctgcgtggaa aagtgggtct gcctggtgtg   420
aaaggtgata aggtccgat gggtcctccg ggtccgaaag gtgatcaggg tgaaaaaggt   480
ccgcgtggtc tgacgggtga accgggcatg cgtggtctgc ctggggcagt tggtgaaccg   540
ggggcaaaag gtgctatggg gccggca                                      567

SEQ ID NO: 8            moltype = DNA  length = 357
FEATURE                 Location/Qualifiers
misc_feature            1..357
                        note = C17C1-DNA
source                  1..357
                        mol_type = other DNA
                        organism = synthetic construct
SEQUENCE: 8
ggtgcagatt ttgcaggtga tctggattat aatgaactgg cagttcgtgt tagcgaaagc    60
atgcagcgtc agggactgct gcaggggaatg gcatataccg ttcagggtcc gccgggtcag   120
ccgggtcctc aaggtcctcc tggtattagc aaagttttta gtgcatattc aaacgtgacg   180
gcagatctga tggattttttt tcagacgtat ggtgcaattc agggtcctcc tgggcaaaaa   240
ggtgaaatgg gtacacctgg tccgaaaggc gatcgtggtc cggccggtcc gccgggccac   300
cctggtcctc ctggccctcg tggtcataaa ggtgagaaag gtgataaagg tgatcaa      357

SEQ ID NO: 9            moltype = AA  length = 1497
FEATURE                 Location/Qualifiers
REGION                  1..1497
                        note = COL17A1
source                  1..1497
                        mol_type = protein
                        organism = synthetic construct
SEQUENCE: 9
MDVTKKNKRD GTEVTERIVT ETVTTRLTSL PPKGGTSNGY AKTASLGGGS RLEKQSLTHG    60
SSGYINSTGS TRGHASTSSY RRAHSPASTL PNSPGSTFER KTHVTRHAYE GSSSGNSSPE   120
YPRKEFASSS TRGRSQTRES EIRVRLQSAS PSTRWTELDD VKRLLKGSRS ASVSPTRNSS   180
NTLPIPKKGT VETKIVTASS QSVSGTYDAT ILDANLPSHV WSSTLPAGSS MGTYHNNMTT   240
QSSSLLNTNA YSAGSVFGVP NNMASCSPTL HPGLSTSSSV FGMQNNLAPS LTTLSHGTTT   300
TSTAYGVKKN MPQSPAAVNT GVSTSAACTT SVQSDDLLHK DCKFLILEKD NTPAKKEMEL   360
LIMTKDSGKV FTASPASIAA TSFSEDTLKK EKQAAYNADS GLKAEANGDL KTVSTKGKTT   420
TADIHSYGSS GGGGSGGGGG VGGAGGGPWG PAPAWCPCGS CCSWWKWLLG LLLTWLLLLG   480
LLFGLIALAE EVRKLKARVD ELERIRRSIL PYGDSMDRIE KDRLQGMAPA AGADLDKIGL   540
HSDSQEELWM FVRKKLMMEQ ENGNLRGSPG PKGDMGSPGP KGDRGFPGTP GIPGPLGHPG   600
PQGPKGQKGS VGDPGMEGPM GQRGREGPMG PRGEAGPPGS GEKGERGAAG EPGPHGPPGV   660
PGSVGPKGSS GSPGPQGPPG PVGLQGLRGE VGLPGVKGDK GPMGPPGPKG DQGEKGPRGL   720
TGEPGMRGLP GAVGEPGAKG AMGPAGPDGH QGPRGEQGLT GMPGIRGPPG PSGDPGKPGL   780
TGPQGPQGLP GTPGRPGIKG EPGAPGKIVT SEGSSMLTVP GPPGPPGAMG PPGPPGAPGP   840
AGPAGLPGHQ EVLNLQGPPG PPGPRGPPGP SIPGPPGPRG PPGEGLPGPP GPPGSFLSNS   900
ETFLSGPPGP PGPPGPKGDQ GPPGPRGHQG EQGLPGFSTS GSSSFGLNLQ GPPGPPGPQG   960
PKGDKGDPGV PGALGIPSGP SEGGSSSTMY VSGPPGPPGP PGPPGSISSS GQEIQQYISE  1020
YMQSDSIRSY LSGVQGPPGP PGPPGPVTTI TGETFDYSEL ASHVVSYLRT SGYGVSLFSS  1080
SISSSEDILAV LQRDDVRQYL RQYLMGPRGP PGPPGASGDG SLLSLDYAEL SSRILSYMSS  1140
SGISIGLPGP PGPPGLPGTS YEELLSLLRG SEFRGIVGPP GPPGPPGIPG NVWSSISVED  1200
LSSYLHTAGL SFIPGPPGPP GPPGPRGPPG VSGALATYAA ENSDSFRSEL ISYLTSPDVR  1260
SFIVGPPGPP GPQGPPGDSR LLSTDASHSR GSSSSSHSSS VRRGSSYSSS MSTGGGGAGS  1320
LGAGGAFGEA AGDRGPYGTD IGPGGGYGAA AEGGMYAGNG GLLGADFAGD LDYNELAVRV  1380
SESMQRQGLL QGMAYTVQGP PGQPGPQGPP GISKVFSAYS NVTADLMDFF QTYGAIQGPP  1440
GQKGEMGTPG PKGDRGPAGP PGHPGPPGPR GHKGEKGDKG DQVYAGRRRR RSIAVKP     1497
```

HUMAN COLLAGEN 17-TYPE POLYPEPTIDE, PRODUCTION METHOD THEREFOR AND USE THEREOF

CROSS-REFERENCE TO RELATED APPLICATION

This application is a continuation application of U.S. patent application Ser. No. 17/761,992 filed on Mar. 18, 2022, issued as U.S. Pat. No. 12,043,657 on Jul. 23, 2024, which is the U.S. National Stage Entry of PCT application No: PCT/CN2020/123600, filed on Oct. 26, 2020, which claims the priority of the Chinese patent application No. 201911051106.3 filed on Oct. 31, 2019. The disclosed contents of the above application are all hereby incorporated by reference in their entirety.

REFERENCE TO A SEQUENCE LISTING

This application contains a Sequence Listing which has been submitted electronically in XML (eXtensible Markup Language) and is incorporated herein by reference in its entirety. Said XML copy, created on May 16, 2024, is named S2335-700240 Sequence Listing.xml.

TECHNICAL FIELD

The present invention belongs to the technical field of genetic engineering, and relates to polypeptides, production methods and uses thereof.

BACKGROUND ART

Collagen Collagen is generally white, transparent, and unbranched fibrils, which is the basic support for skin and bones. It can account for 25% to 35% of the total amount of protein. Collagen is mainly distributed in the skin, blood vessels, bones, tendons, teeth and cartilage among other parts of the human body, serving as the main matrix and scaffolds of these tissues, and it protects and connects various tissues, and plays important physiological functions in the body. Therefore, collagen can be widely utilized in industries such as medicine and cosmetics.

The collagen products currently on the market are all taken from tissues of animals such as pigs, bovines, and fish. Although the collagen of certain animals is highly similar to that of humans, it is still difficult to avoid the risk of viral infection and sensitization. At present, a small amount of animal-derived collagen has been used in cosmetics, but it is difficult to be widely used in medical equipment or sophisticated tissue engineering products to perform the original biological function of collagen. Moreover, collagen prepared by conventional methods generally has a strong coagulation function, which leads to a great risk of thrombosis when it is used in certain tissue engineering products, thereby greatly limiting its extensive and in-depth application.

The traditional method of producing collagen is to process animal-derived tissues by utilizing acid, alkali, and enzymatic hydrolysis to extract collagen derivatives. The collagen extracted by these methods has lost its original biological activity and cannot be used in the field of biomedicine to perform its real function. Some research institutions in China and abroad express human-derived collagen in vitro through conventional recombinant expression methods, but the production cost is usually too high and the production cycle is too long to be put into large-scale production. Therefore, there is an urgent need in the market for a collagen material with excellent biomaterial properties, a high degree of amino acid sequence homology with the human body, and which can be prepared in large quantities in an industrialized system.

Type 17 Human Collagen

From a structural point of view, the structure of natural collagen in the human body is very complicated, which makes it extremely difficult to express and prepare in large quantities human-derived collagen by conventional means. The most common structural feature of collagen is a triple helix structure formed by three peptide chains, that is, three A peptide chains form a protein in a right-handed supercoiled manner, and such a triple helix region is called a collagen region. Each A peptide chain in molecular structure is composed of repetitive Gly-X-Y (X and Y represent any amino acid residues other than Gly, X is often Pro, and Y is often Hyp) peptide fragments that form a left-handed helix, and under the interaction of amino acid residues, 3 A peptide chains are centered on the same axis and form a stable triple helix structure in a right-handed supercoiled manner. Therefore, it is generaly difficult for collagen sequences to spontaneously combine to form a stable triple helix structure in order to perform biological functions. Such difficulties severely hinder the development and production of human collagen.

The human body contains 28 different types of collagen, which are divided into common fibrous collagen and uncommon non-fibrous collagen. Type I, Type II and Type III in human skin belong to fibrous collagen. Among non-fibrous collagen, a very important subtype of collagen is type 17 collagen, collagen XVII, (encoded by the COL17A1 gene in the human body). Type 17 collagen is a homotrimer formed by the combination of three COL17A1 chains, with a single chain molecular weight of 180 kDa. It comprises a spherical intracellular domain of 70 kDa, a transmembrane domain and an extracellular collagen domain of 120 kDa, which has robust thermal stability. Recent studies have confirmed that type 17 collagen is an important component of hemidesmosome in epidermal stem cells in the human body and plays an important role in both cell aging and skin differentiation. However, humans currently have very limited understanding of the structure and function of non-fibrous collagen, especially for type 17 collagen.

The inventor has studied the structure and function of collagen in depth for many years. In particular, for the first time in the world, he analyzed the new atomic structure of multiple segments of human collagen, and posted it to the international protein structure database for public display, and accumulated rich research experience. Through repeated explorations, the inventor has successfully achieved the recombinant expression of several extracellular functional regions of type 17 collagen, and found that it has excellent biomaterial properties, its preparation method is simple, easy to expand production, and can be widely used in industries such as medicine and cosmetics.

SUMMARY OF THE INVENTION

The present invention is based in part on the following findings:

The polypeptides C17A3, C17B3 and C17C1 of the present invention have comparable or greater cell adhesion effects compared with existing human collagen, and the polypeptides C17A3, C17B3 and C17C1 exist in water-soluble form after being expressed in host cells, and the preparation method is simple, easy to expand production.

Against the drawbacks of the prior art shown in the background art, the present invention provides:

Item 1. A polypeptide comprising 63-1496 continuous amino acid residues in SEQ ID No. 9, wherein the polypeptide has cell adhesion activity.

Item 2. A polypeptide, wherein the polypeptide comprises or consists of the sequence shown in $(A)_m$, wherein each A is selected from the amino acid sequence shown in any one of SEQ ID No. 1, SEQ ID No. 2 and SEQ ID No. 3, or the amino acid sequence with one or more, such as 2, 3, 4 or 5 amino acid residues substituted, added, or deleted in any one of SEQ ID No. 1, SEQ ID No. 2 and SEQ ID No. 3, or the sequence with a sequence identity of 83%, 84%, 85%, 86%, 87%, 88%, 89%, 90%, 91%, 92%, 93%, 94%, 95%, 96% or 97% to the amino acid sequence shown in any one of SEQ ID No. 1, SEQ ID No. 2 and SEQ ID No. 3; m is an integer between 1-10, wherein each A is the same or different and adjacent two As are directly linked by a peptide bond or linked by more than one amino acid residues; wherein the polypeptide has cell adhesion activity. The interval described herein includes endpoints, for example, between 1 to 10 includes 1, 2, 3, 4, 5, 6, 7, 8, 9, 10, that is, m can be 1, 2, 3, 4, 5, 6, 7, 8, 9 or 10.

Item 3. The polypeptide of Item 1 or 2, wherein the polypeptide comprises or consists of the amino acid sequence shown in SEQ ID No. 1, SEQ ID No. 2, SEQ ID No. 3, SEQ ID No. 4, or SEQ ID No. 6.

Item 4. A polynucleotide encoding the polypeptide according to any one of Items 1-3, preferably, the polynucleotide comprising or consisting of nucleotide sequence shown in SEQ ID No. 5, SEQ ID No. 7, or SEQ ID No. 8.

Item 5. An expression vector comprising the polynucleotide according to Item 4.

Item 6. A host cell comprising the expression vector according to Item 5 or expressing the polypeptide according to any one of Items 1-3, wherein the host cell is preferably an *Escherichia coli* (*E. coli*) cell.

Item 7. A method for preparing the polypeptide according to any one of Items 1-3, which comprises:
(1) culturing the host cell according to Item 6 in a production medium;
(2) isolating the polypeptide according to any one of Items 1-3 from the host cell.

Item 8. A composition comprising the polypeptide according to any one of Items 1-3 or the polypeptide prepared according to the method of Item 7.

Item 9. A article comprising the polypeptide according to any one of Items 1-3 or the polypeptide prepared according to the method of Item 7 or the composition according to Item 8, wherein the article is a pharmaceutical composition, a medical device, a tissue engineering product, cosmetics, or a health product, preferably the pharmaceutical composition is a topical preparation, preferably a topical smear preparation, such as a topical gel or a topical infiltration preparation; wherein preferably the topical gel further comprises pharmaceutically acceptable carriers, and the topical infiltration preparation further comprises sterile medical cotton balls.

Item 10. Use of the polypeptide according to any one of Items 1-3 or the polypeptide prepared by the method of Item 7, the polynucleotide of Item 4, the expression vector of Item 5, the host cell of Item 6, or the composition of Item 8 in the preparation of articles, preferably medical devices, tissue engineering products, cosmetics, and health products.

Compared with the prior art, the present invention has the following characteristics:

(1) The type 17 human collagen sequence selected for the first time in the present invention is a sequence optimized for long-term screening;
(2) The *E. coli* expression system is employed, which is suitable for large-scale amplification, and one round of fermentation can be completed in 20 hours. The production cost is very low. Due to the codon optimization of *E. coli* for the gene sequence and the selection of 2×YT medium, the output is in tremendous amount;
(3) The recombinant human-derived collagen produced has very good hydrophilicity and stability, and its amino acid composition is 100% identical to the corresponding part of the amino acid sequence of natural collagen. It will not cause immune rejection and allergic reaction when applied to the human body, and can be widely used in biomedicine and cosmetics industry;
(4) The product of the present invention has undergone activity detection and has a biological activity that can reach or exceed the biological activity of natural protein in the human body, which can exercise the function of the natural protein in the human body to achieve the purpose of real product application;
(5) The technical design of the present invention can effectively reduce the risk of coagulation of collagen when used in the human body, while retaining the high cell adhesion activity of collagen, and has a wide range of tissue engineering application prospects.

DETAILED EMBODIMENTS

A further description is provided below to facilitate the understanding of the present invention.

As used herein, "medical devices" refer to instruments, equipment, appliances, in vitro diagnostic reagents and calibrators, materials, and other similar or related items used directly or indirectly on the human body.

As used herein, "tissue engineering products" refer to products used for tissue engineering. Tissue engineering is an emerging discipline that combines cell biology and material science to construct tissues or organs in vitro or in vivo.

As used herein, "isolation" refers to isolating target polypeptides from cultured host cells, for example, to disrupt the host cells and purify the target polypeptides. In the case that the purified target polypeptides have purification tags, such as Trx or His tag, "insolation" also includes the removal of the Trx or His tag by restriction digestion.

"Pharmaceutically acceptable carriers" are well known to those skilled in the art, and those skilled in the art can select pharmaceutically acceptable carriers suitable for use in the compositions or articles of the present invention. For example, pharmaceutically acceptable carriers include, but are not limited to: buffers such as phosphoric acid, citric acid and other organic acids; antioxidants, including ascorbic acid and methionine; preservatives (such as octadecyl dimethyl benzyl ammonium chloride; hexamethonium chloride; benzalkonium chloride; benzethonium chloride; phenol, butanol or benzyl alcohol; alkyl parabens such as methyl paraben or propyl paraben; catechol; resorcine; cyclohexanol; 3-pentanol; and m-cresol); low molecular weight (less than about 10 residues) polypeptides; proteins, such as serum albumin, gelatin, or immunoglobulin; hydrophilic polymers such as polyvinylpyrrolidone; amino acids such as glycine, glutamine, asparagine, histidine, arginine or lysine; monosaccharides, disaccharides, and other carbohydrates, including glucose, mannose or dextrin; chelating agents such as EDTA; sugars such as sucrose, mannitol, trehalose, or sorbitol; salt-forming counterions such as sodium; metal complexes (such as Zn-protein complexes); and/or non-ionic surfactants such as polyethylene glycol (PEG).

In the present invention, the sequence of human type 17 collagen COL17A1 is selected for screening and optimization. The sequence of the human collagen type 17 is the NCBI reference sequence: Q9UMD9.3 (SEQ ID No. 9).

(SEQ ID No. 9)
MDVTKKNKRDGTEVTERIVTETVTTRLTSLPPKGGTSNGYAKTASLGGGS

RLEKQSLTHGSSGYINSTGSTRGHASTSSYRRAHSPASTLPNSPGSTFER

KTHVTRHAYEGSSSGNSSPEYPRKEFASSSTRGRSQTRESEIRVRLQSAS

PSTRWTELDDVKRLLKGSRSASVSPTRNSSNTLPIPKKGTVETKIVTASS

QSVSGTYDATILDANLPSHVWSSTLPAGSSMGTYHNNMTTQSSSLLNTNA

YSAGSVFGVPNNMASCSPTLHPGLSTSSSVFGMQNNLAPSLTTLSHGTTT

-continued
TSTAYGVKKNMPQSPAAVNTGVSTSAACTTSVQSDDLLHKDCKFLILEKD

NTPAKKEMELLIMTKDSGKVFTASPASIAATSFSEDTLKKEKQAAYNADS

GLKAEANGDLKTVSTKGKTTTADIHSYGSSGGGGSGGGGVGGAGGGPWG

PAPAWCPCGSCCSWWKWLLGLLLTWLLLLGLLFGLIALAEEVRKLKARVD

ELERIRRSILPYGDSMDRIEKDRLQGMAPAAGADLDKIGLHSDSQEELWM

FVRKKLMMEQENGNLRGSPGPKGDMGSPGPKGDRGFPGTPGIPGPLGHPG

PQGPKGQKGSVGDPGMEGPMGQRGREGPMGPRGEAGPPGSGEKGERGAAG

EPGPHGPPGVPGSVGPKGSSGSPGPQGPPGPVGLQGLRGEVGLPGVKGDK

GPMGPPGPKGDQGEKGPRGLTGEPGMRGLPGAVGEPGAKGAMGPAGPDGH

QGPRGEQGLTGMPGIRGPPGPSGDPGKPGLTGPQGPQGLPGTPGRPGIKG

EPGAPGKIVTSEGSSMLTVPGPPGPPGAMGPPGPPGAPGPAGPAGLPGHQ

EVLNLQGPPGPPGPRGPPGPSIPGPPGPRGPPGEGLPGPPGPPGSFLSNS

ETFLSGPPGPPGPPGPKGDQGPPGPRGHQGEQGLPGFSTSGSSSFGLNLQ

GPPGPPGPQGPKGDKGDPGVPGALGIPSGPSEGGSSSTMYVSGPPGPPGP

PGPPGSISSSGQEIQQYISEYMQSDSIRSYLSGVQGPPGPPGPPGPVTTI

TGETFDYSELASHVVSYLRTSGYGVSLFSSSISSEDILAVLQRDDVRQYL

RQYLMGPRGPPGPPGASGDGSLLSLDYAELSSRILSYMSSSGISIGLPGP

PGPPGLPGTSYEELLSLLRGSEFRGIVGPPGPPGPPGIPGNVWSSISVED

LSSYLHTAGLSFIPGPPGPPGPPGPRGPPGVSGALATYAAENSDSFRSEL

ISYLTSPDVRSFIVGPPGPPGPQGPPGDSRLLSTDASHSRGSSSSSHSSS

VRRGSSYSSSMSTGGGGAGSLGAGGAFGEAAGDRGPYGTDIGPGGGYGAA

AEGGMYAGNGGLLGADFAGDLDYNELAVRVSESMQRQGLLQGMAYTVQGP

PGQPGPQGPPGISKVFSAYSNVTADLMDFFQTYGAIQGPPGQKGEMGTPG

PKGDRGPAGPPGHPGPPGPRGHKGEKGDKGDQVYAGRRRRRSIAVKP

The bold underlined part in the sequence described above is the amino acid sequence selected in the present invention. The applicant found through a lot of research that the selected sequence described above has strong water solubility, high recombinant expression yield, simple purification process, and achieves better cell adhesion than commercial human collagen or other sequences in SEQ ID No. 9, with a variety of excellent biological material properties. In the present invention, the polypeptide is not the full-length sequence of SEQ ID No. 9.

The present invention is based in part on the following findings: a polypeptide comprising at least 63 continuous amino acid residues in SEQ ID No. 9 can have better biomaterial properties than commercial human collagen, as demonstrated in the examples. Those skilled in the art can appropriately select the continuous amino acid residues constituting the recombinant collagen. For example, the length of continuous amino acid residues may be 48-100, 50-72, 54-57 and 48-72 among others.

In the present invention, the sequences of several specific amino acid regions have been detected:

(1) C17A:
(SEQ ID No. 1)
GSPGPKGDMGSPGPKGDRGFPGTPGIPGPLGHPGPQGPKGQKGSVGDPGM

EGPMGQRGREGPMGPRGEA;

(2) C17B:
(SEQ ID No. 2)
GLQGLRGEVGLPGVKGDKGPMGPPGPKGDQGEKGPRGLTGEPGMRGLPGA

VGEPGAKGAMGPA;

(3) C17C:
(SEQ ID No. 3)
GADFAGDLDYNELAVRVSESMQRQGLLQGMAYTVQGPPGQPGPQGPPGIS

KVFSAYSNVTADLMDFFQTYGAIQGPPGQKGEMGTPGPKGDRGPAGPPGH

PGPPGPRGHKGEKGDKGDQ;

The polypeptide herein can be recombinant human-derived collagen C17A3, which is a triple repeat sequence of C17A, including 207 amino acids, and the basic repeat unit is: GSPGPKGDMGSPGPKGDRGFPGTPGIPGPLGHPG PQGPKGQKGSVGDPG MEGPMGQRGREGPMGPR-GEA (SEQ ID No. 1), which is human collagen type 17 peptide fragment.

The amino acid sequence of C17A3 is as follows:

(SEQ ID No. 4)
GSPGPKGDMGSPGPKGDRGFPGTPGIPGPLGHPGPQGPKGQKGSVGDPGM

EGPMGQRGREGPMGPRGEAGSPGPKGDMGSPGPKGDRGFPGTPGIPGPLG

HPGPQGPKGQKGSVGDPGMEGPMGQRGREGPMGPRGEAGSPGPKGDMGSP

GPKGDRGFPGTPGIPGPLGHPGPQGPKGQKGSVGDPGMEGPMGQRGREGP

MGPRGEA.

The DNA sequence of C17A3 is as follows:

(SEQ ID No. 5)
GGTAGCCCAGGTCCAAAAGGTGATATGGGAAGCCCAGGTCCGAAAGGTGA

TCGTGGTTTTCCGGGTACACCAGGTATTCCGGGTCCACTGGGTCATCCAG

GTCCGCAAGGTCCGAAAGGCCAGAAAGGTAGCGTGGGTGATCCGGGTATG

GAAGGGCCTATGGGGCAGCGTGGGCGTGAAGGGCCGATGGGTCCGCGTGG

TGAAGCAGGTAGCCCGGGGCCTAAAGGGGATATGGGGAGTCCGGGTCCGA

AAGGGGATCGTGGATTTCCGGGTACGCCGGGTATCCCGGGTCCGCTGGGT

CATCCGGGTCCGCAAGGGCCTAAAGGTCAGAAAGGTAGTGTGGGTGATCC

TGGTATGGAAGGTCCGATGGGTCAGCGTGGTCGTGAGGGTCCGATGGGAC

CGCGTGGTGAGGCTGGTAGCCCTGGTCCGAAAGGAGATATGGGGTAGCCCG

GGTCCGAAAGGTGACCGTGGTTTTCCTGGTACACCGGGTATTCCAGGGCC

TCTGGGTCATCCTGGTCCTCAGGGTCCGAAAGGTCAGAAAGGGAGTGTGG

GAGATCCGGGTATGGAGGGTCCGATGGGGCAGCGCGGTCGTGAAGGTCCG

ATGGGCCCGCGTGGTGAAGCC.

The polypeptide herein may be human-derived collagen C17B3, which is a triple repeat sequence of C17B, including 189 amino acids, and the basic repeat unit is: GLQGLR-GEVGLPGVKGDKGPMGPPGPKGDQGEKGPRGLT-GEPGMRGLP GAVGEPGAKGAMGPA (SEQ ID No. 2), which is human collagen type 17 peptide fragment.

The amino acid sequence of C17B3 is as follows:

(SEQ ID No. 6)
GLQGLRGEVGLPGVKGDKGPMGPPGPKGDQGEKGPRGLTGEPGMRGLPGA

VGEPGAKGAMGPAGLQGLRGEVGLPGVKGDKGPMGPPGPKGDQGEKGPRG

LTGEPGMRGLPGAVGEPGAKGAMGPAGLQGLRGEVGLPGVKGDKGPMGPP

GPKGDQGEKGPRGLTGEPGMRGLPGAVGEPGAKGAMGPA.

The DNA sequence of C17B3 is as follows:

(SEQ ID No. 7)
GGTCTGCAGGGTCTGCGTGGTGAAGTAGGACTGCCGGGTGTGAAAGGAGA

TAAAGGACCAATGGGTCCACCAGGACCAAAAGGAGATCAAGGAGAAAAAG

GACCACGTGGTCTGACAGGTGAACCGGGTATGCGTGGGCTGCCGGGAGCA

GTTGGAGAACCGGGAGCAAAAGGAGCAATGGGTCCAGCAGGACTGCAGGG

TCTGCGCGGTGAAGTGGGACTGCCTGGTGTTAAAGGGGATAAAGGGCCGA

TGGGTCCGCCGGGTCCGAAAGGAGATCAGGGAGAAAAAGGGCCGCGTGGT

CTGACCGGTGAACCGGGAATGCGTGGTCTGCCGGGGGCTGTGGGTGAGCC

AGGTGCAAAAGGTGCAATGGGTCCTGCAGGTCTGCAAGGACTGCGTGGAG

AAGTGGGTCTGCCTGGTGTGAAAGGTGATAAAGGTCCGATGGGTCCTCCG

GGTCCGAAAGGTGATCAGGGTGAAAAAGGTCCGCGTGGTCTGACGGGTGA

ACCGGGCATGCGTGGTCTGCCTGGGGCAGTTGGTGAACCGGGGGCAAAAG

GTGCTATGGGGCCGGCA.

The polypeptide herein can be recombinant human-derived collagen C17C1, which is a repeat sequence of C17C, including 119 amino acids, and the basic repeat unit is: GADFAGDLDYNELAVRVSESMQRQGLLQGMAYTV QGPPGQPGPQGPPGI SKVFSAYSNVTADLMDFF QTY-GAIQGPPGQKGEMGTPGPKGDRGPAGPP GHPGP PG PRGHKGEKGDKGDQ (SEQ ID No. 3), which is the human collagen type 17 peptide.

The amino acid sequence of C17C1 is as follows:

(SEQ ID No. 3)
GADFAGDLDYNELAVRVSESMQRQGLLQGMAYTVQGPPGQPGPQGPPGIS

KVFSAYSNVTADLMDFFQTYGAIQGPPGQKGEMGTPGPKGDRGPAGPPGH

PGPPGPRGHKGEKGDKGDQ.

The DNA sequence of C17C1 is as follows:

(SEQ ID No. 8)
GGTGCAGATTTTGCAGGTGATCTGGATTATAATGAACTGGCAGTTCGTGT

TAGCGAAAGCATGCAGCGTCAGGGACTGCTGCAGGGAATGGCATATACCG

TTCAGGGTCCGCCGGGTCAGCCGGGTCCTCAAGGTCCTCCTGGTATTAGC

AAAGTTTTTAGTGCATATTCAAACGTGACGGCAGATCTGATGGATTTTTT

TCAGACGTATGGTGCAATTCAGGGTCCTCCTGGGCAAAAAGGTGAAATGG

GTACACCTGGTCCGAAAGGCGATCGTGGTCCGGCCGGTCCGCCGGGCCAC

-continued
CCTGGTCCTCCTGGCCCTCGTGGTCATAAAGGTGAGAAAGGTGATAAAGG

TGATCAA.

Herein, the polypeptide may include the amino acid sequence shown in any one of SEQ ID No. 1, SEQ ID No. 2, SEQ ID No. 3, SEQ ID No. 4, SEQ ID No. 6 and SEQ ID NO. 9 with substitutions, additions, deletions or insertions of one or more, preferably 2, 3, 4 or 5 amino acid residues, or amino acid sequence with a sequence identity of 83%, 84%, 85%, 86%, 87%, 88%, 89%, 90%, 91%, 92%, 93%, 94%, 95%, 96% or 97% to the amino acid sequence shown in any one of SEQ ID No. 1, SEQ ID No. 2, SEQ ID No. 3, SEQ ID No. 4, SEQ ID No. 6 and SEQ ID No. 9. The "percentage identity of amino acid sequence" relative to the reference polypeptide sequence is defined as the percentage of amino acid residues in the candidate sequence that are identical to the amino acid residues in the reference polypeptide sequence after gaps are introduced when necessary to obtain the maximum percentage of sequence identity when the candidate sequence is aligned with the reference polypeptide sequence, without any conservative substitutions are considered part of sequence identity. The alignment used to determine the percentage identity of amino acid sequences can be achieved in various ways known to those skilled in the art, for example, using publicly available computer software, such as BLAST, BLAST-2, ALIGN or Megalign (DNASTAR) software. Those skilled in the art can determine suitable parameters for aligning sequences, which includes any algorithms required to achieve maximum alignment over the full length of the sequences being compared.

Amino acid addition refers to adding amino acids to the C- or N-terminus of the amino acid sequences, such as any one of SEQ ID No. 1, SEQ ID No. 2, SEQ ID No. 3, SEQ ID No. 4, SEQ ID No. 6, and SEQ ID NO. 9, provided that the polypeptide has collagen characteristics and cell adhesion activity.

Amino acid substitution refers to replacing a certain amino acid residue in a certain position by another amino acid residue in the amino acid sequences, such as the sequence of any one of SEQ ID No. 1, SEQ ID No. 2, SEQ ID No. 3, SEQ ID No. 4, SEQ ID No. 6, and SEQ ID NO 9, provided that the polypeptide has collagen characteristics and cell adhesion activity.

Amino acid insertion refers to inserting amino acid residues to appropriate positions of the amino acid sequences, such as the sequence of any one of SEQ ID No. 1, SEQ ID No. 2, SEQ ID No. 3, SEQ ID No. 4, SEQ ID No. 6 and SEQ ID NO. 9. The inserted amino acid residues can either be adjacent to each other in whole or in part, or none of the inserted amino acids are adjacent to each other, provided that the polypeptide has collagen characteristics and cell adhesion activity.

Amino acid deletion refers to deleting 1, 2 or more than 3 amino acids from amino acid sequences, such as the sequence of any one of SEQ ID No. 1, SEQ ID No. 2, SEQ ID No. 3, SEQ ID No. 4, SEQ ID No. 6, and SEQ ID NO. 9, provided that the polypeptide has collagen characteristics and cell adhesion activity.

In the present invention, substitutions may be conservative amino acid substitutions, which refer to 3, more preferably 2 amino acids or 1 amino acid replaced by amino acids with similar or comparable properties, as compared with any one of the amino acid sequences of SEQ ID No. 1, SEQ ID No. 2, SEQ ID No. 3, SEQ ID No. 4, SEQ ID No. 6, and SEQ ID NO. 9, to form peptides. These conservative variant peptides can be produced by performing amino acid substitutions according to Table 1.

TABLE 1

Conservative Substitution of Amino Acids

| Original Residue | Representative Substitution | Preferred Substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

All amino acids in the polypeptide sequence herein can be L type amino acids, within which one or more (such as 2-5, 2-4 or 2-3) amino acids can also be replaced with amino acids with D type conformation, artificially modified amino acids, and rare amino acids existed in nature among others, in order to improve the bioavailability, stability, and/or antiviral activity of the polypeptides. Among them, D type amino acids refer to the amino acids corresponding to the L type amino acids that make up proteins; artificially modified amino acids refer to common L type amino acids making up proteins that have been modified by methylation, phosphorylation, etc.; rare amino acids existed in nature include uncommon amino acids that make up proteins, and amino acids that do not make up proteins, such as 5-hydroxylysine, methylhistidine, y aminobutyric acid, homoserine, etc.

In the present invention, recombining human-derived collagen can be carried out by conventional methods in the art. For example, it can be produced in the following steps: (1) constructing genetically engineered bacteria of E. coli; (2) fermentation culturing the genetically engineered bacteria of E. coli; (3) inducing and expressing the recombinant human-derived collagen; and (4) purifying and optionally restriction digest the recombinant human-derived collagen.

In Step (1), the construction of genetically engineered bacteria of E. coli can be carried out as follows: (1) codon optimizing and splicing recombining DNA fragments in the gene helix region of human-derived type 17 collagen by PCR method to finally obtain target gene fragments; (2) inserting the obtained target gene fragments into PET-32a expression vectors to obtain recombinant expression plasmids; (3) transforming the recombinant expression plasmids into E. coli competent cells BL21 (DE3), and screening to obtain positive genetically engineered bacteria of E. coli.

In Steps (2) and (3), the fermentation culture of the genetically engineered bacteria of E. coli and the induction and expression of recombinant human-derived collagen can be carried out as follows: (1) picking the optimized single colony of the genetically engineered bacteria of E. coli from the LAB plate, placing which in 10 ml of LB medium and culturing at 37° C., 220 rpm for 12-16 hours; (2) amplification culturing the bacterial solution inoculated into 2×YT medium at a ratio of 1:100, and culturing at 37° C. for about 3 hours. When the $OD_{600}$ is 0.4-0.6, adding IPTG at a final concentration of 0.5 mM for induction, culturing at 16° C. for additional 20 hours, and collecting the bacteria by centrifugation.

In Step (4), the purification and restriction digestion of recombinant human-derived collagen polypeptides can be carried out as follows: (1) resuspending the bacteria in phosphate buffer (40 mM $NaH_2PO_3$, 500 mM NaCl, pH 7.8), disrupting ultrasonically, and collecting the supernatant by centrifugation; (2) utilizing NI-NTA affinity column to bind recombinant human-derived collagen, rinsing the impure proteins with 10 mM imidazole prior to adding Tev protease (Tobacco Etch Virus enzyme), digesting on the column at 4° C. for 16 hours, and finally obtaining the target collagen polypeptides.

The host cells may be eukaryotic cells, such as fungi and yeast, or prokaryotic cells, such as Enterobacteriaceae, such as *Escherichia coli*. It should be understood that those skilled in the art can replace the above-mentioned *E. coli* strains with other expression strains as host cells.

EXAMPLES

The following examples are provided to illustrate the invention. Those skilled in the art should understand that the examples are merely illustrative and not restrictive. The present invention is limited solely by the scope of the appended claims.

Example 1: Construction, Expression and Purification of Recombinant Human-Derived Collagen Polypeptides Construction and Expression of C17A3 Gene Expression Vector 1. The full-length gene sequence of human-derived collagen C17A3 used in Example 1 is shown in SEQ ID No. 5. This sequence has been codon optimized for the codons of *E. coli*.

2. The full length of C17A3 gene is 621 bp. According to the optimized C17A3 codon gene sequence SEQ ID No. 5, Beijing Shengyuan Kemeng Gene Biotechnology Co., Ltd. is entrusted to synthesize the gene fragment, and after linking the synthesized C17A3 gene fragment to Tev protease restriction sites, the gene fragment is inserted to the PET32a expression vector (provided by the Institute of Biophysics, Chinese Academy of Sciences) through the Kpn I and Xho I restriction sites. The successfully constructed expression plasmid is transformed into *E. coli* competent cells BL21 (DE3) (Merck Company). The specific process is as follows: 1: taking 1l of this plasmid to 100 μl of *E. coli* competent cells BL21 (DE3), and letting it stand on ice for 30 min. 2: heat shocking the mixture in a 42° C. water bath for 90 s, then quickly placing it on ice and letting it stand for 2 min. 3: adding 600 μl of non-resistant LB to the mixture and culturing for 1 hour at 37° C., 220 rpm. 4: taking 200 μl of the bacterial solution and evenly spreading it on the ampicillin resistance-containing LB plate (10 g/L peptone, 5 g/L yeastextract, 10 g/L sodium chloride, 15 g/L agar, 100 μg/ml ampicillin antibiotics). 5: culturing the plate upside down in a 37° C. incubator for about 20 h until growing out clear and visible colonies.

3. Picking a single colony from the transformed LB plate and culturing it in 10 ml LB (containing 100 μg/ml ampicillin antibiotics) medium for 12 h-16 h, then transferring it to 2×YT medium (16 g/L peptone, 10 g/L yeast extract, 5 g/L sodium chloride) at the ratio of 1:100 for amplification culturing, culturing at 37° C., 220 rpm until the $OD_{600}$ of the bacterial solution is 0.4-0.6, adding IPTG (Sigma Company, Cat. No.: I5502-1G) at a final concentration of 0.5 mM for inducing expression. The inducing conditions are 18° C., 180 rpm for 20 h. Finally, collecting the bacteria by centrifugation, and storing at −20° C. or immediately proceeding to the next step of purification.

4. Resuspending (1 L) the bacterial precipitation by using about 50 ml of phosphate buffer (pH 7.8) (40 mM sodium dihydrogen phosphate, 500 mM sodium chloride), and disrupting the bacteria by utilizing a high-pressure bacterium disrupting instrument (SCIENTZ BIO) prior to centrifuging at 13000 rpm for 30 min to fully isolate the soluble protein from the inclusion bodies.

5. Equilibrating the Ni-NTA (Qiagen company, Cat. No.: 30210) affinity column with 5 column volumes of binding buffer (40 mM $NaH_2PO_3$, 500 mM NaCl, pH 7.8). Then adding the protein supernatant and incubating at 4° C. for 0.5-1 h to allow the target recombinant protein fully bind to the column material. Then rinsing the impure proteins with 200 ml of washing buffer containing 10 mM imidazole (10 mM imidazole, 40 mM $NaH_2PO_3$, 500 mM NaCl, pH 7.8) (Sigma Company). If Trx-tagged target protein is needed, an elution buffer (250 mM imidazole, 40 mM $NaH_2PO_3$, 500 mM NaCl, pH 7.8) can be used directly to elute the target protein Trx-C17A3. If the Trx-tagged target protein needs to be removed, an appropriate amount of TEV protease with His tag can be added. After incubating at 4° C. for 16 h, collecting the flow-through fluid, which is the target collagen C17A3 with the carrier protein Trx removed.

6. The anion exchange column can be used for rapid purification of the target protein. Dialyzing the target protein into buffer A (20 mM Tris, 15 mM NaCl, pH 8.0), letting it flow through the anion exchange column Hitrap Q (GE Healthcare), and gradient eluting with buffer B (20 mM Tris, 1 M NaCl, pH 8.0), collecting different elution fractions to detect protein. Dialyzing the obtained target protein product overnight, and lyophilizing it into dry powder for later use.

7. Detecting the molecular weight and purity of the obtained C17A3 protein by SDS-PAGE. The specific process is: taking 40 μl of purified protein solution, adding 10 μl of 5× protein loading buffer (250 mM Tris-HCl (pH: 6.8), 10% SDS, 0.5% bromophenol blue, 50% glycerol, 5% β-mercaptoethanol), boiling in 100° C. boiling water at for 10 min, then adding 10 μl per well to SDS-PAGE protein gel, running at 80V for 2 h, and staining the protein with Coomassie Brilliant Blue Staining Solution (0.1% Coomassie Brilliant Blue R-250, 25% Isopropanol, 10% acetic acid glacial) for 20 min, then utilizing protein decolorizing solution (10% acetic acid, 5% ethanol) for decolorization. Finally, measuring the protein activity in comparison with human natural collagen.

Construction and Expression of C17B3 Gene Expression Vector

1. The full-length gene sequence of human-derived collagen C17B3 used in Example 2 is shown in SEQ ID No. 7. This sequence has been codon optimized for the codons of *E. coli*.

2. The full length of C17B3 gene is 567 bp. According to the optimized C17B3 codon gene sequence SEQ ID No. 7, Beijing Shengyuan Kemeng Gene Biotechnology Co., Ltd. is entrusted to synthesize the gene fragment, and after linking the synthesized C17B3 gene fragment to Tev protease restriction sites, the gene fragment is inserted to the PET32a expression vector (provided by the Institute of Biophysics, Chinese Academy of Sciences) through the Kpn I and Xho I restriction sites. The successfully constructed expression plasmid is transformed into E. coli competent cells BL21 (DE3) (Merck Company). The specific process is as follows: 1: taking 1 µl of this plasmid to 100 µl of E. coli competent cells BL21 (DE3), and letting it stand on ice for 30 min. 2: heat shocking the mixture in a 42° C. water bath for 90 s, then quickly placing it on ice and letting it stand for 2 min. 3: adding 600 µl of non-resistant LB to the mixture and culturing for 1 hour at 37° C., 220 rpm. 4: taking 200 µl of the bacterial solution and evenly spreading it on the ampicillin resistance-containing LB plate (10 g/L peptone, 5 g/L yeast extract, 10 g/L sodium chloride, 15 g/L agar, 100 µg/ml ampicillin antibiotics). 5: culturing the plate upside down in a 37° C. incubator for about 20 h until growing out clear and visible colonies.

3. Picking a single colony from the transformed LB plate and culturing it in 10 ml LB (containing 100 µg/ml ampicillin antibiotics) medium for 12 h-16 h, then transferring it to 2×YT medium (16 g/L peptone, 10 g/L yeast extract, 5 g/L sodium chloride) at the ratio of 1:100 for amplification culturing, culturing at 37° C., 220 rpm until the $OD_{600}$ of the bacterial solution is 0.4-0.6, adding IPTG (Sigma Company, Cat. No.: I5502-1G) at a final concentration of 0.5 mM for inducing expression. The inducing conditions are 18° C., 180 rpm for 20 h. Finally, collecting the bacteria by centrifugation, and storing at −20° C. or immediately proceeding to the next step of purification.

4. Resuspending (1 L) the bacterial precipitation by using about 50 ml of phosphate buffer (pH 7.8) (40 mM sodium dihydrogen phosphate, 500 mM sodium chloride), and disrupting the bacteria by utilizing a high-pressure bacterium disrupting instrument (SCIENTZ BIO) prior to centrifuging at 13000 rpm for 30 min to fully isolate the soluble protein from the inclusion bodies.

5. Equilibrating the Ni-NTA (Qiagen company, Cat. No.: 30210) affinity column with 5 column volumes of binding buffer (40 mM $NaH_2PO_3$, 500 mM NaCl, pH 7.8). Then adding the protein supernatant and incubating at 4° C. for 0.5-1 h to allow the target recombinant protein fully bind to the column material. Then rinsing the impure proteins with 200 ml of washing buffer containing 10 mM imidazole (10 mM imidazole, 40 mM $NaH_2PO_3$, 500 mM NaCl, pH 7.8) (Sigma Company). If Trx-tagged target protein is needed, an elution buffer (250 mM imidazole, 40 mM $NaH_2PO_3$, 500 mM NaCl, pH 7.8) can be used directly to elute the target protein Trx-C17B3. If the Trx-tagged target protein needs to be removed, an appropriate amount of TEV protease with His tag can be added. After incubating at 4° C. for 16 h, collecting the flow-through fluid, which is the target collagen C17B3 with the carrier protein Trx removed.

6. The anion exchange column can be used for rapid purification of the target protein. Dialyzing the target protein into buffer A (20 mM Tris, 15 mM NaCl, pH 8.0), letting it flow through the anion exchange column Hitrap Q (GE Healthcare), and gradient eluting with buffer B (20 mM Tris, 1 M NaCl, pH 8.0), collecting different elution fractions to detect protein. Dialyzing the obtained target protein product overnight, and lyophilizing it into dry powder for later use.

7. Detecting the molecular weight and purity of the obtained C17B3 protein by SDS-PAGE. The specific process is: taking 40 µl of purified protein solution, adding 10 µl of 5× protein loading buffer (250 mM Tris-HCl (pH: 6.8), 10% SDS, 0.5% bromophenol blue, 50% glycerol, 5% β-mercaptoethanol), boiling in 100° C. boiling water at for 10 min, then adding 10 µl per well to SDS-PAGE protein gel, running at 80V for 2 h, and staining the protein with Coomassie Brilliant Blue Staining Solution (0.1% Coomassie Brilliant Blue R-250, 25% Isopropanol, 10% acetic acid glacial) for 20 min, then utilizing protein decolorizing solution (10% acetic acid, 5% ethanol) for decolorization. Finally, measuring the protein activity in comparison with human natural collagen.

Construction and Expression of C17C1 Gene Expression Vector

1. The full-length gene sequence of human-derived collagen C17C1 used in Example 2 is shown in SEQ ID No. 8. This sequence has been codon optimized for the codons of E. coli.

2. The full length of C17C1 gene is 357 bp. According to the optimized C17C1 codon gene sequence SEQ ID No. 8, Beijing Shengyuan Kemeng Gene Biotechnology Co., Ltd. is entrusted to synthesize the gene fragment, and after linking the synthesized C17C1 gene fragment to Tev protease restriction sites, the gene fragment is inserted to the PET32a expression vector (provided by the Institute of Biophysics, Chinese Academy of Sciences) through the Kpn I and Xho I restriction sites. The successfully constructed expression plasmid is transformed into E. coli competent cells BL21 (DE3) (Merck Company). The specific process is as follows: 1: taking 1 µl of this plasmid to 100 µl of E. coli competent cells BL21 (DE3), and letting it stand on ice for 30 min. 2: heat shocking the mixture in a 42° C. water bath for 90 s, then quickly placing it on ice and letting it stand for 2 min. 3: adding 600 µl of non-resistant LB to the mixture and culturing for 1 hour at 37° C., 220 rpm. 4: taking 200 µl of the bacterial solution and evenly spreading it on the ampicillin resistance-containing LB plate (10 g/L peptone, 5 g/L yeast extract, 10 g/L sodium chloride, 15 g/L agar, 100 µg/ml ampicillin antibiotics). 5: culturing the plate upside down in a 37° C. incubator for about 20 h until growing out clear and visible colonies.

3. Picking a single colony from the transformed LB plate and culturing it in 10 ml LB (containing 100 µg/ml ampicillin antibiotics) medium for 12 h-16 h, then transferring it to 2×YT medium (16 g/L peptone, 10 g/L yeast extract, 5 g/L sodium chloride) at the ratio of 1:100 for amplification culturing, culturing at 37° C., 220 rpm until the $OD_{600}$ of the bacterial solution is 0.4-0.6, adding IPTG (Sigma Company, Cat. No.: I5502-1G) at a final concentration of 0.5 mM for inducing expression. The inducing conditions are 18° C., 180 rpm for 20 h. Finally, collecting the bacteria by centrifugation, and storing at −20° C. or immediately proceeding to the next step of purification.

4. Resuspending (1 L) the bacterial precipitation by using about 50 ml of phosphate buffer (pH 7.8) (40 mM sodium dihydrogen phosphate, 500 mM sodium chloride), and disrupting the bacteria by utilizing a high-pressure bacterium disrupting instrument (SCIENTZ BIO) prior to centrifuging at 13000 rpm for 30 min to fully isolate the soluble protein from the inclusion bodies.

5. Equilibrating the Ni-NTA (Qiagen company, Cat. No.: 30210) affinity column with 5 column volumes of binding buffer (40 mM $NaH_2PO_3$, 500 mM NaCl, pH 7.8). Then adding the protein supernatant and incubating at 4° C. for 0.5-1 h to allow the target recombinant protein fully bind to the column material. Then rinsing the impure proteins with 200 ml of washing buffer containing 10 mM imidazole (10 mM imidazole, 40 mM $NaH_2PO_3$, 500 mM NaCl, pH 7.8) (Sigma Company). If Trx-tagged target protein is needed, an elution buffer (250 mM imidazole, 40 mM $NaH_2PO_3$, 500 mM NaCl, pH 7.8) can be used directly to elute the target protein Trx-C17C1. If the Trx-tagged target protein needs to be removed, an appropriate amount of TEV protease with His tag can be added. After incubating at 4° C. for 16 h, collecting the flow-through fluid, which is the target collagen C17C1 with the carrier protein Trx removed.

6. The anion exchange column can be used for rapid purification of the target protein. Dialyzing the target protein into buffer A (20 mM Tris, 15 mM NaCl, pH 8.0), letting it flow through the anion exchange column Hitrap Q (GE Healthcare), and gradient eluting with buffer B (20 mM Tris, 1 M NaCl, pH 8.0), collecting different elution fractions to detect protein. Dialyzing the obtained target protein product overnight, and lyophilizing it into dry powder for later use.

7. Detecting the molecular weight and purity of the obtained C17C1 protein by SDS-PAGE. The specific process is: taking 40 μl of purified protein solution, adding 10 μl of 5× protein loading buffer (250 mM Tris-HCl (pH: 6.8), 10% SDS, 0.5% bromophenol blue, 50% glycerol, 5% β-mercaptoethanol), boiling in 100° C. boiling water at for 10 min, then adding 10 μl per well to SDS-PAGE protein gel, running at 80V for 2 h, and staining the protein with Coomassie Brilliant Blue Staining Solution (0.1% Coomassie Brilliant Blue R-250, 25% Isopropanol, 10% acetic acid glacial) for 20 min, then utilizing protein decolorizing solution (10% acetic acid, 5% ethanol) for decolorization. Finally, measuring the protein activity in comparison with human natural collagen.

Results

Figure 1:
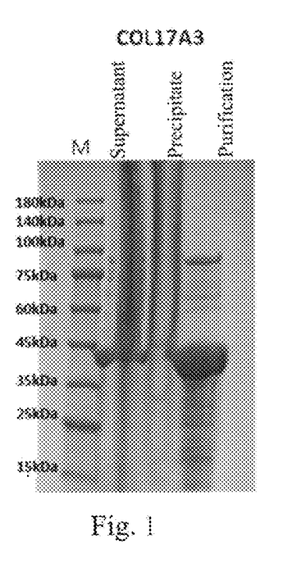
FIG. 1 is a protein electrophoresis diagram obtained after expression and purification of the Trx-C17A3 protein of the present invention; the molecular weight of the Trx-C17A3 protein detected by electrophoresis is about 42 kDa.
Figure 2:
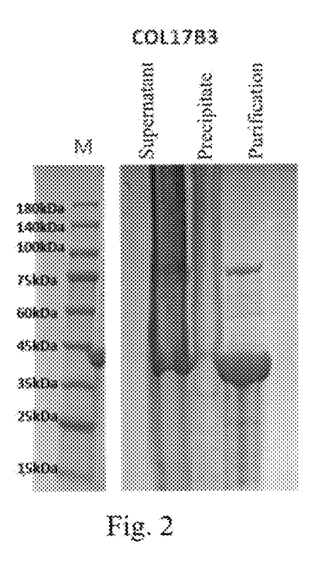
FIG. 2 is a protein electrophoresis diagram obtained after expression and purification of the Trx-C17B3 protein of the present invention; the molecular weight of the Trx-C17B3 protein detected by electrophoresis is about 40 kDa.
Figure 3:
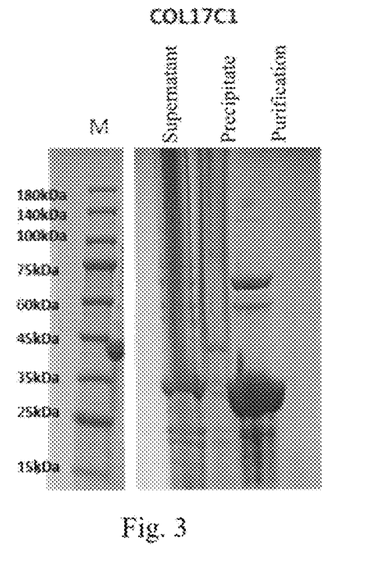
FIG. 3 is a protein electrophoresis diagram obtained after expression and purification of the Trx-C17C1 protein of the present invention; the molecular weight of the Trx-C17C1 protein detected by electrophoresis is about 32 kDa.

Electrophoresis diagrams of FIG. 1-FIG. 3 respectively show that Trx-C17A3, Trx-C17B3 and Trx-C17C1 fusion proteins with apparent molecular weights of 42 kDa, 40 kDa and 32 kDa are obtained.

Figure 4:
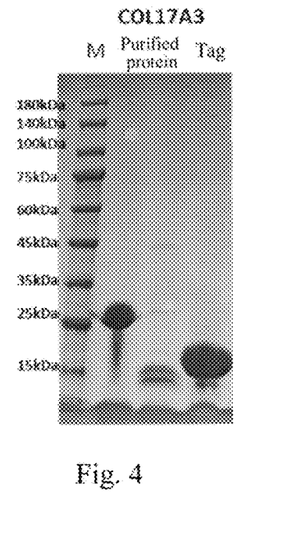
FIG. 4 is an electrophoresis diagram of the target protein C17A3 protein obtained after the expression of Trx-C17A3 protein, through restriction digestion to remove the Trx tag and ion exchange purification; the molecular weight of the C17A3 protein detected by electrophoresis is about 25 kDa, which corresponds to the protein with amino acid sequence of SEQ ID No. 4.
Figure 5:
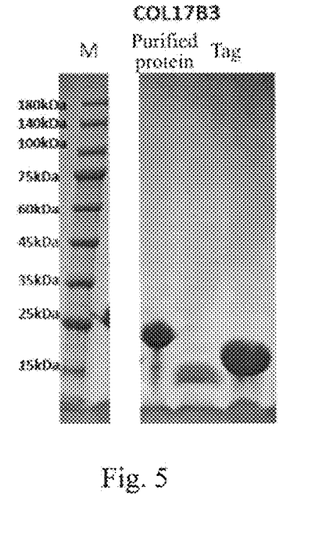
FIG. 5 is an electrophoresis diagram of the target protein C17B3 protein obtained after the expression of Trx-C17B3 protein, through restriction digestion to remove the Trx tag and ion exchange purification; the molecular weight of the C17B3 protein detected by electrophoresis is about 23 kDa, which corresponds to the protein with amino acid sequence of SEQ ID No. 6.
Figure 6:
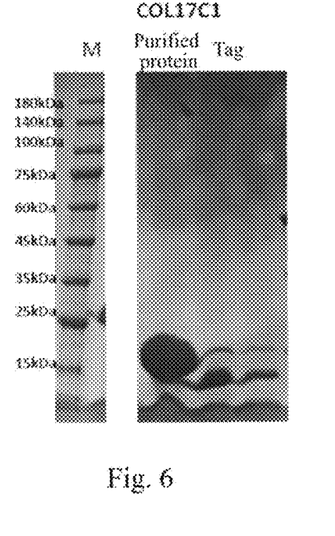
FIG. 6 is an electrophoresis diagram of the target protein C17C1 protein obtained after the expression of Trx-C17C1 protein, through restriction digestion to remove Trx tag and ion exchange purification; the molecular weight of C17C1 protein detected by electrophoresis is about 16 kDa, which corresponds to the protein with amino acid sequence of SEQ ID No.3.

Electrophoresis diagrams of FIG. 4-FIG. 6 respectively show that C17A3, C17B3 and C17C1 fusion proteins with apparent molecular weights of 25 kDa, 23 kDa, and 16 kDa are obtained.

Example 2: Detection of Cell Adhesion Activity of C17A3, C17B3, and C17C1 Proteins For the detection method of collagen activity, please refer to the literature Juming Yao, Satoshi Yanagisawa, Tetsuo Asakura, Design, Expression and Characterization of Collagen-Like Proteins Based on the Cell Adhesive and Crosslinking Sequences Derived from Native Collagens, J Biochem. 136, 643-649 (2004). The specific implementation method is as follows:

1. Detecting the concentration of the protein sample to be detected including human collagen control (Sigma, C7774), C17A3, C17A1 (SEQ ID No. 1, prepared by the same method as C17A3), C17B3, C17B1 (SEQ ID No. 2, prepare by the same method as C17B3), and C17C1 protein samples by utilizing the ultraviolet (UV) absorption method. Specifically, determining the UV absorption of the samples at 215 nm and 225 nm, and calculating the protein concentrations by the empirical formula C(μg/mL)=144×(A215-A225). It should be noted that it needs to be detected when A215<1.5. The principle of this method is to determine the characteristic absorption of peptide bonds under far UV light, which is not affected by the content of chromophore, has less interference substances, and is simple to operate. It is suitable for detecting human collagen and its analogs that are not colored by Coomassie Brilliant Blue. (The reference is Walker JM. The Protein Protocols Handbook, second edition. Humana Press. 43-45). After detecting the protein concentrations, adjusting the concentrations of all detected proteins to 0.5 mg/ml with PBS.

2. Adding 100 μl of various protein solutions and PBS solution blank control to the 96-well plate, and letting it stand at room temperature for 60 min.

3. Adding $10^5$ well-cultured 3T3 cells (from Teacher Tong Pei, Tsinghua University) into each well, and incubating at 37° C. for 60 minutes.

4. Washing each well with PBS 4 times.

5. Detecting the absorbance at $OD_{492nm}$ with LDH detection kit (Roche, 04744926001). The absorbance at $OD_{492nm}$ can reflect the cell adhesion activity of collagen or its fragments. The higher the cell adhesion activity of the protein, the more it can provide cells with a high-quality external environment in a short time, helping cells adhere to the wall.

Figure 7:
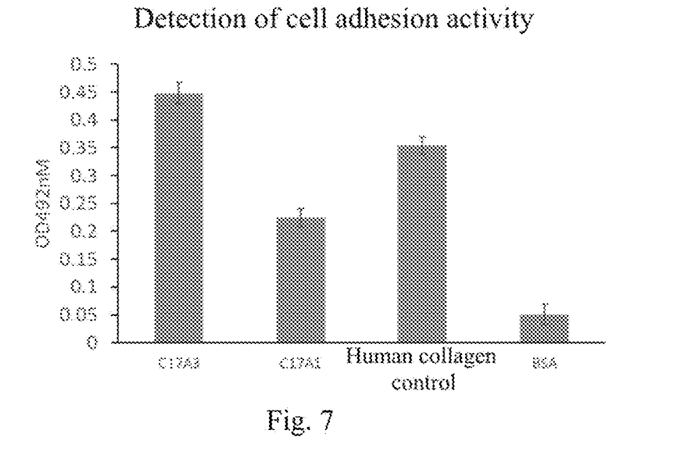
FIG. 7 shows the biological activity detection results of the C17A3 protein of the present invention compared with the C17A1 protein (SEQ ID No. 1) and human collagen.
Figure 8:
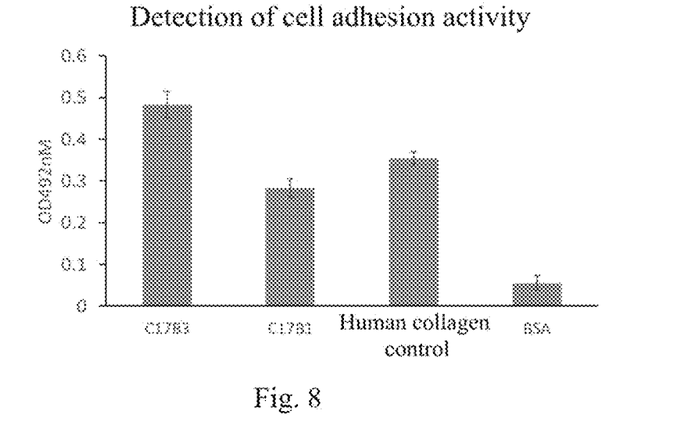
FIG. 8 shows the biological activity detection results of the C17B3 protein of the present invention compared with the C17B1 protein (SEQ ID No. 2) and human collagen.
Figure 9:
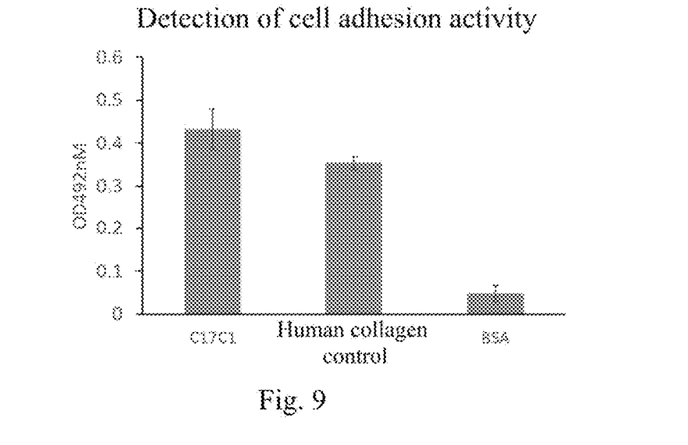
FIG. 9 shows the biological activity detection results of the C17C1 protein of the present invention compared with human collagen.

See FIGS. 7 to 9 for results. FIGS. 7 to 9 are plotted based on the average and standard error of $OD_{492nm}$ from three parallel experiments.

The results of FIGS. 7 to 9 show that the three human recombinant collagens (i.e., C17A3, C17B3, and C17C1) all have good cell adhesion activity compared with commercial human collagen.

```
Sequences
(C17A)
                                            SEQ ID NO. 1
GSPGPKGDMGSPGPKGDRGFPGTPGIPGPLGHPGPQGPKGQKGSV

GDPGMEGPMGQRGREGPMGPRGEA (C17B)
                                            SEQ ID NO. 2
GLQGLRGEVGLPGVKGDKGPMGPPGPKGDQGEKGPRGLTGEPGMR

GLPGAVGEPGAKGAMGPA (C17C1)
                                            SEQ ID NO. 3
GADFAGDLDYNELAVRVSESMQRQGLLQGMAYTVQGPPGQPGPQG

PPGISKVFSAYSNVTADLMDFFQTYGAIQGPPGQKGEMGTPGPKG

DRGPAGPPGHPGPPGPRGHKGEKGDKGDQ (C17A3)
                                            SEQ ID NO. 4
GSPGPKGDMGSPGPKGDRGFPGTPGIPGPLGHPGPQGPKGQKGSV

GDPGMEGPMGQRGREGPMGPRGEAGSPGPKGDMGSPGPKGDRGFP

GTPGIPGPLGHPGPQGPKGQKGSVGDPGMEGPMGQRGREGPMGPR

GEAGSPGPKGDMGSPGPKGDRGFPGTPGIPGPLGHPGPQGPKGQK

GSVGDPGMEGPMGQRGREGPMGPRGEA (C17A3-DNA)
                                            SEQ ID NO. 5
GGTAGCCCAGGTCCAAAAGGTGATATGGGAAGCCCAGGTCCGAAA

GGTGATCGTGGTTTTCCGGGTACACCAGGTATTCCGGGTCCACTG

GGTCATCCAGGTCCGCAAGGTCCGAAAGGCCAGAAAGGTAGCGTG

GGTGATCCGGGTATGGAAGGGCCTATGGGGCAGCGTGGGCGTGAA

GGGCCGATGGGTCCGCGTGGTGAAGCAGGTAGCCCGGGGCCTAAA

GGGGATATGGGGAGTCCGGGTCCGAAAGGGGATCGTGGATTTCCG

GGTACGCCGGGTATCCCGGGTCCGCTGGGTCATCCGGGTCCGCAA

GGGCCTAAAGGTCAGAAAGGTAGTGTGGGTGATCCTGGTATGGAA

GGTCCGATGGGTCAGCGTGGTCGTGAGGGTCCGATGGGACCGCGT

GGTGAGGCTGGTAGCCCTGGTCCGAAAGGAGATATGGGTAGCCCG
```

```
GGTCCGAAAGGTGACCGTGGTTTTCCTGGTACACCGGGTATTCCA
GGGCCTCTGGGTCATCCTGGTCCTCAGGGTCCGAAAGGTCAGAAA
GGGAGTGTGGGAGATCCGGGTATGGAGGGTCCGATGGGGCAGCGC
GGTCGTGAAGGTCCGATGGGCCCGCGTGGTGAAGCC (C17B3)
                                              SEQ ID NO. 6
GLQGLRGEVGLPGVKGDKGPMGPPGPKGDQGEKGPRGLTGEPGMR
GLPGAVGEPGAKGAMGPAGLQGLRGEVGLPGVKGDKGPMGPPGPK
GDQGEKGPRGLTGEPGMRGLPGAVGEPGAKGAMGPAGLQGLRGEV
GLPGVKGDKGPMGPPGPKGDQGEKGPRGLTGEPGMRGLPGAVGEP
GAKGAMGPA (C17B3-DNA)
                                              SEQ ID NO. 7
GGTCTGCAGGGTCTGCGTGGTGAAGTAGGACTGCCGGGTGTGAAA
GGAGATAAAGGACCAATGGGTCCACCAGGACCAAAAGGAGATCAA
GGAGAAAAAGGACCACGTGGTCTGACAGGTGAACCGGGTATGCGT
GGGCTGCCGGGAGCAGTTGGAGAACCGGGAGCAAAAGGAGCAATG
GGTCCAGCAGGACTGCAGGGTCTGCGCGGTGAAGTGGGACTGCCT
GGTGTTAAAGGGGATAAAGGGCCGATGGGTCCGCCGGGTCCGAAA
GGAGATCAGGGAGAAAAAGGGCCGCGTGGTCTGACCGGTGAACCG
GGAATGCGTGGTCTGCCGGGGGCTGTGGGTGAGCCAGGTGCAAAA
GGTGCAATGGGTCCTGCAGGTCTGCAAGGACTGCGTGGAGAAGTG
GGTCTGCCTGGTGTGAAAGGTGATAAAGGTCCGATGGGTCCTCCG
GGTCCGAAAGGTGATCAGGGTGAAAAAGGTCCGCGTGGTCTGACG
GGTGAACCGGGCATGCGTGGTCTGCCTGGGGCAGTTGGTGAACCG
GGGGCAAAAGGTGCTATGGGGCCGGCA (C17C1-DNA)
                                              SEQ ID NO. 8
GGTGCAGATTTTGCAGGTGATCTGGATTATAATGAACTGGCAGTT
CGTGTTAGCGAAAGCATGCAGCGTCAGGGACTGCTGCAGGGAATG
GCATATACCGTTCAGGGTCCGCCGGGTCAGCCGGGTCCTCAAGGT
CCTCCTGGTATTAGCAAAGTTTTTAGTGCATATTCAAACGTGACG
GCAGATCTGATGGATTTTTTTCAGACGTATGGTGCAATTCAGGGT
CCTCCTGGGCAAAAAGGTGAAATGGGTACACCTGGTCCGAAAGGC
GATCGTGGTCCGGCCGGTCCGCCGGGCCACCCTGGTCCTCCTGGC
CCTCGTGGTCATAAAGGTGAGAAAGGTGATAAAGGTGATCAA (COL17A1)
                                              SEQ ID NO. 9
MDVTKKNKRDGTEVTERIVTETVTTRLTSLPPKGGTSNGYAKTAS
LGGGSRLEKQSLTHGSSGYINSTGSTRGHASTSSYRRAHSPASTL
PNSPGSTFERKTHVTRHAYEGSSSGNSSPEYPRKEFASSSTRGRS
QTRESEIRVRLQSASPSTRWTELDDVKRLLKGSRSASVSPTRNSS
NTLPIPKKGTVETKIVTASSQSVSGTYDATILDNLPSHVWSSTL
PAGSSMGTYHNNMTTQSSSLLNTNAYSAGSVFGVPNNMASCSPTL
HPGLSTSSSVFGMQNNLAPSLTTLSHGTTTTSTAYGVKKNMPQSP
AAVNTGVSTSAACTTSVQSDDLLHKDCKFLILEKDNTPAKKEMEL
LIMTKDSGKVFTASPASIAATSFSEDTLKKEKQAAYNADSGLKAE
ANGDLKTVSTKGKTTTADIHSYGSSGGGGSGGGGGVGGAGGGPWG
PAPAWCPCGSCCSWWKWLLGLLLTWLLLLGLLFGLIALAEEVRKL
KARVDELERIRRSILPYGDSMDRIEKDRLQGMAPAAGADLDKIGL
HSDSQEELWMFVRKKLMMEQENGNLRGSPGPKGDMGSPGPKGDRG
FPGTPGIPGPLGHPGPQGPKGQKGSVGDPGMEGPMGQRGREGPMG
PRGEAGPPGSGEKGERGAAGEPGPHGPPGVPGSVGPKGSSGSPGP
QGPPGPVGLQGLRGEVGLPGVKGDKGPMGPPGPKGDQGEKGPRGL
TGEPGMRGLPGAVGEPGAKGAMGPAGPDGHQGPRGEQGLTGMPGI
RGPPGPSGDPGKGPGLTGPQGPQGLPGTPGRPGIKGEPGAPGKIVT
SEGSSMLTVPGPPGPPGAMGPPGPPGAPGPAGPAGLPGHQEVLNL
QGPPGPPGPRGPPGPSIPGPPGPRGPPGEGLPGPPGPPGSFLSNS
ETFLSGPPGPPGPPGPKGDQGPPGPRGHQGEQGLPGFSTSGSSSF
GLNLQGPPGPPGQGPKGDKGDPGVPGALGIPSGPSEGGSSSTMY
VSGPPGPPGPPGPPGSISSSGQEIQQYISEYMQSDSIRSYLSGVQ
GPPGPPGPPGPVTTITGETFDYSELASHVVSYLRTSGYGVSLFSS
SISSEDILAVLQRDDVRQYLRQYLMGPRGPPGPPGASGDGSLLSL
DYAELSSRILSYMSSSGISIGLPGPPGPPGLPGTSYEELLSLLRG
SEFRGIVGPPGPPGPPGIPGNVWSSISVEDLSSYLHTAGLSFIPG
PPGPPGPPGPRGPPGVSGALATYAAENSDSFRSELISYLTSPDVR
SFIVGPPGPPGPQGPPGDSRLLSTDASHSRGSSSSSHSSSVRRGS
SYSSSMSTGGGGAGSLGAGGAFGEAAGDRGPYGTDIGPGGGYAA
AEGGMYAGNGGLLGADFAGDLDYNELAVRVSESMQRQGLLQGMAY
TVQGPPGQPGPQGPPGISKVFSAYSNVTADLMDFFQTYGAIQGPP
GQKGEMGTPGPKGDRGPAGPPGHPGPPGPRGHKGEKGDKGDQVYA
GRRRRRSIAVKP
```

---

The invention claimed is:

1. A polypeptide having cell adhesion activity, wherein the polypeptide consists of an amino acid sequence selected from a group consisting of the amino acid sequence of SEQ ID NO: 3, an amino acid sequence having a sequence identity of at least 83% to SEQ ID NO: 3 and an amino acid sequence having 1-10 amino acid substitutions, additions, or deletions in SEQ ID NO: 3.

2. The polypeptide of claim 1, wherein the polypeptide consists of the amino acid sequence of SEQ ID NO: 3.

3. The polypeptide of claim 1, wherein the polypeptide consists of an amino acid sequence having a sequence identity of at least 88% to SEQ ID NO: 3.

4. The polypeptide of claim 3, wherein the polypeptide consists of an amino acid sequence having a sequence identity of at least 92% to SEQ ID NO: 3.

5. The polypeptide of claim 4, wherein the polypeptide consists of an amino acid sequence having a sequence identity of at least 95% to SEQ ID NO: 3.

6. The polypeptide of claim 5, wherein the polypeptide consists of an amino acid sequence having a sequence identity of at least 97% to SEQ ID NO: 3.

7. A composition comprising the polypeptide according to claim 1.

8. An article comprising the polypeptide according to claim 1, wherein the article is a pharmaceutical composition, a medical device, a tissue engineering product, a cosmetic, or a health product.

9. The article of claim 8, wherein the pharmaceutical composition is a topical preparation.

10. The article of claim 9, wherein the topical preparation is a topical smear preparation.

11. The article of claim 10, wherein the topical preparation is a topical gel or a topical infiltration preparation.

12. The article of claim 11, wherein the topical gel further comprises a pharmaceutically acceptable carrier, and the topical infiltration preparation further comprises a sterile medical cotton ball.

13. A method of preparing an article, comprising utilizing the polypeptide according to claim 1.

14. The method of claim 13, wherein the article is a medical device, a tissue engineering product, a cosmetic, or a health product.

15. A polynucleotide encoding the polypeptide according to claim 1.

16. The polynucleotide of claim 15, wherein the polynucleotide comprises or consists of the nucleotide sequence of SEQ ID NO: 8.

17. An expression vector comprising the polynucleotide according to claim 15.

18. A host cell comprising the expression vector according to claim 15.

19. The host cell of claim 18, wherein the host cell is an *E. coli* cell.

20. A method for preparing a polypeptide, which comprises:
 (1) culturing the host cell according to claim 19 in a production medium; and
 (2) isolating the polypeptide from the host cell.

\* \* \* \* \*